US012773428B2

(12) United States Patent
Halum

(10) Patent No.: US 12,773,428 B2
(45) **Date of Patent: *Oct. 27, 2026**

(54) PRIMED MUSCLE PROGENITOR CELLS AND USES THEREOF

(71) Applicant: Purdue Research Foundation, West Lafayette, IN (US)

(72) Inventor: Stacey L Halum, Indianapolis, IN (US)

(73) Assignee: Purdue Research Foundation, West Lafayette, IN (US)

( * ) Notice: Subject to any disclaimer, the term of this patent is extended or adjusted under 35 U.S.C. 154(b) by 1041 days.

This patent is subject to a terminal disclaimer.

(21) Appl. No.: 17/552,919

(22) Filed: Dec. 16, 2021

(65) Prior Publication Data

US 2022/0110980 A1 Apr. 14, 2022

Related U.S. Application Data

(63) Continuation of application No. 15/964,784, filed on Apr. 27, 2018, now Pat. No. 11,235,005.

(51) Int. Cl.

| | |
|---|---|
| ***A61K 35/34*** | (2015.01) |
| ***A61K 35/30*** | (2015.01) |
| ***A61P 21/00*** | (2006.01) |
| ***A61P 25/00*** | (2006.01) |
| ***A61P 43/00*** | (2006.01) |
| ***C12N 5/077*** | (2010.01) |
| *A61K 31/221* | (2006.01) |
| *A61K 38/18* | (2006.01) |

(52) U.S. Cl.

CPC .............. *A61K 35/34* (2013.01); *A61K 35/30* (2013.01); *A61P 21/00* (2018.01); *A61P 25/00* (2018.01); *A61P 43/00* (2018.01); *C12N 5/0658* (2013.01); *A61K 31/221* (2013.01); *A61K 38/1883* (2013.01); *A61K 2300/00* (2013.01); *C12N 2501/805* (2013.01)

(58) Field of Classification Search

None

See application file for complete search history.

(56) References Cited

U.S. PATENT DOCUMENTS

2013/0177536 A1 7/2013 Mooney et al.

OTHER PUBLICATIONS

Halum, S. L., Naidu, M., Delo, D. M., Atala, A. & Hingtgen, C. M. Injection of Autologous Muscle Stem Cells (Myoblasts) for the Treatment of Vocal Fold Paralysis: A Pilot Study: The Laryngoscope 2007;117, 917-922. PMID: 17473696.

Halum SL, Hiatt KK, Naidu M, Sufyan AS, Clapp DW. Optimization of autologous muscle stem cell survival in the denervated hemilarynx. Laryngoscope 2008;118(7):1308-12.

Dalum SL, McRae BR, Bijangi-Vishehsaraei K, Hiatt K. Neurotrophic Factor-Secreting Autologous Muscle Stem Cell Therapy for the Treatment of Laryngeal Denervation Injury. Laryngoscope 2012;122(11):2482-96. PMID: 22965802.

Yiou R, Yoo JJ, Atala A. Restoration of functional motor units in a rat model of sphincter injury by muscle precursor cell autografts. Transplantation 2003;76(7):1053-60.

Yiou R, Yoo JJ, Atala A. Failure of differentiation into mature myotubes by muscle precursor cells with the side-population phenotype after injection into irreversibly damaged striated urethral sphincter. Transplantation 2005; 80:131-133.

Pagani FD, DerSimonian H, Zawadzka A, et al. Autologous skeletal myoblasts transplanted to ischemia-damaged myocardium in humans: histological analysis of cell survival and differentiation. J Am Coll Cardiol 2003;41: 879-888.

Herreros J, Prosper F, Perez A, et al. Autologous intramyocardial injection of cultured skeletal muscle-derived stem cells in patients with non-acute myocardial infarction. Eur Heart J 2003;24:2012-2020.

Chachques JC, Herreros J, Trainini J, et al. Autologous human serum for cell culture avoids implantation of cardioverter-defibrillators in cellular cardiomyoplasty. Int J Cardiol 2004;95(Suppl 1):S29-S33.

Borisov AB, Dedkov EI, Carlson BM. Differentiation of activated satellite cells in denervated muscle following single fusions in situ and in cell culture. Histochem Cell Biol 2005; 124:13-23.

Lazerges C, Daussin PA, Coulet B, et al. Transplantation of primary satellite cells improves properties of reinnervated skeletal muscles. Muscle Nerve 2004;29:218 -226.

Halum S. Bijangi-Vishehsaraei K, Zhang H, Sowinski J, Bottino M. Stem Cell-Derived Tissue-Engineered Constructs for Hemilaryngeal Reconstruction. Annals of Otology, Rhinology & Laryngology 2014; 123(2):124-134.

Ju YM, Atala A, Yoo JJ, Lee SJ. Acta Biomater. In situ regeneration of skeletal muscle tissue through host cell recruitment. Oct. 2014; 10(10):4332-9.

De Filippo RE, Kornitzer BS, Yoo JJ, Atala A. Penile urethra replacement with autologous cell-seeded tubularized collagen matrices. J Tissue Eng Regen Med. Mar. 2015;9(3):257-64.

Chen CJ et al., Improved neurological Outcome by Intramuscular Injection of Human Amniotic Fluid Derived Stem cells in a Muscle Denervation Model. PLoS ONE 10(5):e0124624.

Dahm et al., Tracheostomy for long-term laryngeal experimentation. Otolaryngol Head Neck Surg. 1998; 118:376-80.

Paniella et al., Glottic Glosing Force Versus Layngeal Adductory Pressure in the Canine Laynx. Annals of Otology, Rhinology & Laryngology, 2017, 126(3):173-178.

*Primary Examiner* — Allison M Fox

(74) *Attorney, Agent, or Firm* — Purdue Research Foundation

(57) ABSTRACT

This invention relates to a method for repairing and reconstructing a damaged or non-functional muscle, in particular to a method and a tool kit using in vitro primed motor endplate-expressing muscle progenitor cells (MPCs) to promote innervation of the damaged or non-functional muscle using an agent without any genetic manipulation. This method is particularly useful for repairing or reconstructing damaged or non-functional head and neck muscles, and urinary detrusor bladder muscle.

7 Claims, 12 Drawing Sheets

PRIMED MUSCLE PROGENITOR CELLS AND USES THEREOF

CROSS-REFERENCE TO RELATED APPLICATIONS

The present U.S. patent application is a continuation of U.S. application Ser. No. 15/964,784, filed on Apr. 27, 2018, which claims the priority benefit of U.S. Provisional Patent Application Ser. No. 62/490,763, filed Apr. 27, 2017. The entire contents of each and all prior application are hereby incorporated by reference in their entireties.

GOVERNMENT SUPPORT CLAUSE

This invention was made with government support under DC014070 awarded by the National Institute of Health. The government has certain rights in the invention.

TECHNICAL FIELD OF THE INVENTION

This invention relates to a method for repairing and reconstructing a damaged or non-functional muscle, in particular to a method and a tool kit using in vitro primed motor endplate-expressing muscle progenitor cells (MPCs) to promote innervation of the damaged or non-functional muscle using an agent without any genetic manipulation.

BACKGROUND OF THE INVENTION

This section introduces aspects that may help facilitate a better understanding of the disclosure. Accordingly, these statements are to be read in this light and are not to be understood as admissions about what is or is not prior art.

A neuromuscular junction is a chemical synapse formed by the contact between a motor neuron and a muscle fiber. It is at the neuromuscular junction that a motor neuron is able to transmit a signal to the muscle fiber, causing muscle contraction. Muscles require innervation to function. In vertebrates, motor neurons release acetylcholine (ACh), a small molecule neurotransmitter, which diffuses across the synaptic cleft and binds to nicotinic acetylcholine receptors (nAChRs) on the cell membrane of the muscle fiber, also known as the sarcolemma. The binding of ACh to the receptor nAChRs can depolarize the muscle fiber, causing a cascade that eventually results in muscle contraction.

A progenitor cell is a biological cell that, like a stem cell, has a tendency to differentiate into a specific type of cell, but is already more specific than a stem cell and is pushed to differentiate into its "target" cell. The most important difference between stem cells and progenitor cells is that stem cells can replicate indefinitely, whereas progenitor cells can divide only a limited number of times. Controversy about the exact definition remains and the concept is still evolving.

Denervation, or the loss of nerve supply in muscle fibers can occur from a variety of causes ranging from serious physical injury to chronic disorders. This disruption in nerve fibers (cells) can cause flaccid paralysis and can eventually lead to severe muscle atrophy. Following a major injury that results in denervation, the physical muscle tissue may heal, but without an adequate, functioning nervous system connection, no effective physical movement can be made. Research in this area has shown that if only certain nerves are damaged, the brain might "rewire" neurological circuitry and resume somewhat normal function. Previously we have shown that how motor endplate expressing MPCs promote self-innervation when used in a tissue engineered construct (Halum, et al., *Annals of Otology, Rhinology & Laryngology,* 23(2):124-134 (2014)) and that MPCs modified with viral vector promote innervation (Halum, et al., *Laryngoscope,* 122(11), 2482-2496 (2012)). However, in cases of muscle denervation, effective physical muscle movement cannot naturally be reversed. The present disclosure provides a potential solution to those unmet needs.

SUMMARY OF THE INVENTION

In some illustrative embodiments, this present invention pertains to a method for preparing primed muscle progenitor cells (MPCs) from a patient with a damaged muscle for repairment or reconstruction of the damaged muscle with enhanced innervation comprising the step of a. acquiring a plurality of moto endplate-expressing muscle progenitor cells (MPCs) from a patient with a damaged muscle; and
b. priming acquired MPCs by incubating said MPCs in the presence of an agent.

In some other illustrative embodiments, this present invention pertains to a method for preparing primed muscle progenitor cells (MPCs) from a patient with a damaged muscle for repairment or reconstruction of the damaged muscle with enhanced innervation disclosed herein, wherein said agent comprises acetylcholine, neuregulin, agrin, or a combination thereof.

In some other illustrative embodiments, this present invention pertains to a method for preparing primed muscle progenitor cells (MPCs) from a patient with a damaged muscle for repairment or reconstruction of the damaged muscle with enhanced innervation disclosed herein, wherein said priming acquired MPCs involves no genetic manipulation.

In some other illustrative embodiments, this present invention pertains to a method for repairing or reconstructing a damaged or non-functioning muscle of a patient with enhanced innervation comprising the steps of:

a. acquiring a plurality of motor endplate-expressing muscle progenitor cells (MPCs) from a patient with a damaged muscle;
b. priming acquired MPCs by incubating said MPCs in the presence of an agent; and
c. introducing the primed MPCs to the damaged muscle of said patient.

In some illustrative embodiments, this present invention pertains to a method for repairing or reconstructing a damaged or non-functioning muscle of a patient with enhanced innervation disclosed herein, wherein said damaged or non-functioning muscle is a denervated head or neck muscle.

In some illustrative embodiments, this present invention pertains to a method for repairing or reconstructing a damaged or non-functioning muscle of a patient with enhanced innervation disclosed herein, wherein said damaged or non-functioning muscle is a denervated laryngeal muscle.

In some illustrative embodiments, this present invention pertains to a method for repairing or reconstructing a damaged or non-functioning muscle of a patient with enhanced innervation disclosed herein, wherein said damaged or non-functioning muscle is a denervated muscle involved in swallowing or voicing.

In some illustrative embodiments, this present invention pertains to a method for repairing or reconstructing a damaged or non-functioning muscle of a patient with enhanced innervation disclosed herein, wherein said MPCs are autologous-derived.

In some illustrative embodiments, this present invention pertains to a method for repairing or reconstructing a damaged or non-functioning muscle of a patient with enhanced innervation disclosed herein, wherein said damaged or non-functioning muscle is a denervated urinary detrusor bladder muscle.

In some illustrative embodiments, this present invention pertains to a method for repairing or reconstructing a damaged or non-functioning muscle of a patient with enhanced innervation disclosed herein, wherein said method provides a treatment for dysphagia.

In some illustrative embodiments, this present invention pertains to a method for repairing or reconstructing a damaged or non-functioning muscle of a patient with enhanced innervation disclosed herein, wherein said priming MPCs involves no genetic manipulation.

In some illustrative embodiments, this present invention pertains to a method for repairing or reconstructing a damaged or non-functioning muscle of a patient with enhanced innervation disclosed herein, wherein said priming MPCs is carried out in vitro to induce the creation of connections between nerve neurons and muscle fibers by incubating in the presence of an agent.

In some illustrative embodiments, this present invention pertains to a method for repairing or reconstructing a damaged or non-functioning muscle of a patient with enhanced innervation disclosed herein, wherein said agent comprises acetylcholine, neuregulin, agrin, or a combination thereof.

In some illustrative embodiments, this present invention pertains to a tool kit for repairing or reconstructing a damaged or non-functioning muscle of a patient with enhanced innervation comprising:

a. a plurality of moto endplate-expressing muscle progenitor cells (MPCs) acquired from a patient with a damaged muscle;
b. priming the acquired MPCs in vitro by incubating in the presence of an agent; and
c. introduction of the primed MPCs to the damaged muscle of said patient.

In some illustrative embodiments, this present invention pertains to a tool kit for repairing or reconstructing a damaged or non-functioning muscle of a patient with enhanced innervation disclosed herein, wherein said damaged or non-functioning muscle is a denervated head or neck muscle.

In some illustrative embodiments, this present invention pertains to a tool kit for repairing or reconstructing a damaged or non-functioning muscle of a patient with enhanced innervation disclosed herein, wherein said damaged or non-functioning muscle is a denervated laryngeal muscle, or a muscle involved in swallowing or voicing.

In some illustrative embodiments, this present invention pertains to a tool kit for repairing or reconstructing a damaged or non-functioning muscle of a patient with enhanced innervation disclosed herein, wherein said damaged muscle or non-functioning is denervated urinary detrusor bladder muscle.

In some illustrative embodiments, this present invention pertains to a tool kit for repairing or reconstructing a damaged or non-functioning muscle of a patient with enhanced innervation disclosed herein, wherein said tool kit is for the treatment of dysphagia.

In some illustrative embodiments, this present invention pertains to a tool kit for repairing or reconstructing a damaged or non-functioning muscle of a patient with enhanced innervation disclosed herein, wherein said priming MPCs is carried out in vitro to induce the creation of connections between nerve neurons and muscle fibers with no genetic manipulation involved.

In some illustrative embodiments, this present invention pertains to a tool kit for repairing or reconstructing a damaged or non-functioning muscle of a patient with enhanced innervation disclosed herein, wherein said agent comprises acetylcholine, neuregulin, agrin, or a combination thereof.

These and other features, aspects and advantages of the present invention will become better understood with reference to the following detailed description and claims.

BRIEF DESCRIPTION OF THE DRAWINGS

FIG. 2A shows immature EGFP+ MPCs (myoblasts) exposed to acetylcholine, neuregulin, and agrin additives express acetylcholine receptors (AChRs) on the surface (gray=alpha-bungarotoxin) but not motor endplates. FIG. 2B shows mature EGFP+ MPCs [myotubes (MTs)] develop when nutrient-deprived myoblasts fuse (arrowheads); upon incubation with acetylcholine, neuregulin, and agrin, MTs express motor endplates on the surface (gray=alpha-bungarotoxin).

FIG. 4A shows that, in the negative PCL control, no active motor unit potentials were detected due to the absence of significant tissue engineered muscle on the implant; insertional activity was reproducible (bracket) when the EMG recording needle was inserted directly into the PCL implant suggesting sparsely populated non-innervated muscle cells had infiltrated the scaffold. FIG. 4B shows that, the MSC group demonstrated low levels of motor unit potentials that fired in synchrony with the contralateral adductor muscle, and no inspiratory activity. FIG. 4C shows that, the MT group demonstrated qualitatively less recruitment upon laryngospasm and no inspiratory activity. FIG. 4D shows that, the MEE group demonstrated bursts of motor unit potentials that were firing with intensity and timing similar to that of the contralateral native adductor muscle complex, and without inspiratory activity. FIG. 4E shows that, the native adductor muscle complex demonstrates bursts of motor unit potentials during laryngospasm, with no active firing on inspiration. FIG. 4F shows that, the PCA demonstrates characteristic inspiratory bursts of activity which were absent in the native adductor complex and the tissue engineered muscle.

FIG. 5A shows an image of 20×; FIG. 5B shows an image of 40×. The green fluorescence indicates successful GFP expression within the cells.

FIG. 6A shows fluorescent microscopy cross sectional image of negative myofiber control for GFP protein; FIG. 6B shows IHC of negative control (longitudinal sectioning) demonstrates no anti-GFP staining; FIG. 6C shows canine thyroarytenoid muscle under fluorescent microscopy in the area of injection demonstrates multiple GFP+ areas (bracket), with the GFP+ fibers [those that had fused with MPCs] demonstrating visibly larger myofiber diameters than adjacent areas, suggesting that the MPC fusion with myofibers enlarges the myofiber diameter; FIG. 6D shows thyroarytenoid muscle injected with GFP+ MPCs on bright field mode microscopy demonstrates peripheral myofiber staining with anti-GFP (arrows; dark brown), with no GFP detected at the center of the myofiber (*), confirming peripheral fusion of the MPCs with the thyroarytenoid myofibers.

FIG. 7A is the control side with rare motor endplates; FIG. 7B MEE side with densely distributed motor endplates (arrows) suggesting the MEE injection group resulted in a stable increased motor endplate expression; FIG. 7C is a magnified (40×) view of the MEE injection group demonstrates a dense complex of innervated motor endplates (bracket) with the neuronal supply depicted with an arrow.

FIGS. 8A-8B, control sides were implanted with normal saline; FIGS. 8C-8D, experimental sides were implanted with MPCs (dog 2, top panel) or MEEs (dog 3, bottom panel). Pre-treatment measurements (open diamonds) have typical curves with plateau at 70-100 Hz. Six-month post-treatment measurements (solid circles) averaged about 60% of initial LAP plateau values for controls, but reached 98% for MPC-implanted dog 2 and 128% for MEE-implanted dog 3.

DETAILED DESCRIPTION OF THE INVENTION

Figure 1:
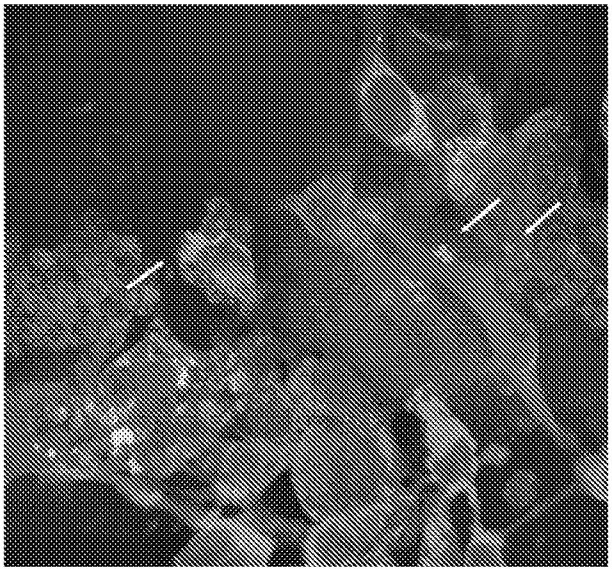
FIG. 1 shows Neuromuscular Junction Formation in Vitro within Co-cultures. Motoneurons are staining positive for motoneuron-specific choline acetyltransferase (ChAT) (light blue) and in areas where they are contacting the MPCs (light orange), the MPCs have formed motor endplates demarcated here in deep orange with motoneuron specific α-bungarotoxin (arrows). Nuclei have been stained with DAPI (deep blue).

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 20%, within 10%, within 5%, or within 1% of a stated value or of a stated limit of a range.

In the present disclosure the term "substantially" can allow for a degree of variability in a value or range, for example, within 80%, within 90%, within 95%, or within 99% of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "patient" includes human and non-human animals such as companion animals (dogs and cats and the like) and livestock animals. Livestock animals are animals raised for food production. The patient to be treated is preferably a mammal, in particular a human being.

A progenitor cell is a biological cell that, like a stem cell, has a tendency to differentiate into a specific type of cell, but is already more specific than a stem cell and is pushed to differentiate into its "target" cell. The most important difference between stem cells and progenitor cells is that stem cells can replicate indefinitely, whereas progenitor cells can divide only a limited number of times. Controversy about the exact definition remains and the concept is still evolving.

Muscle Progenitor Cells (MPCs), also called muscle stem cells, described herein refer to motor endplate-expressing (MEE) muscle progenitor cells. MPCs consist of satellite cells and myoblasts, and have the potential to increase muscle mass and to provide the stimulus for functional reinnervation when implanted into denervated muscles (Chen, C. J., et al., *PLoS One* 2015, 10:e0124624). MPCs can be derived from a small sample of a patient's own tissue, and thus, not rejected by the immune system when they are introduced. Motor endplate is the large and complex end formation by which the axon of a motor neuron establishes synaptic contact with a skeletal muscle fiber (cell). Each muscle fiber forms one endplate.

In some illustrative embodiments, this present invention pertains to a method for preparing primed muscle progenitor cells (MPCs) from a patient with a damaged muscle for repairment or reconstruction of the damaged muscle with enhanced innervation comprising the step of a. acquiring a plurality of moto endplate-expressing muscle progenitor cells (MPCs) from a patient with a damaged muscle; and
b. priming acquired MPCs by incubating said MPCs in the presence of an agent.

In some other illustrative embodiments, this present invention pertains to a method for preparing primed muscle progenitor cells (MPCs) from a patient with a damaged muscle for repairment or reconstruction of the damaged muscle with enhanced innervation disclosed herein, wherein said agent comprises acetylcholine, neuregulin, agrin, or a combination thereof.

In some other illustrative embodiments, this present invention pertains to a method for preparing primed muscle progenitor cells (MPCs) from a patient with a damaged muscle for repairment or reconstruction of the damaged muscle with enhanced innervation disclosed herein, wherein said priming acquired MPCs involves no genetic manipulation.

In some other illustrative embodiments, this present invention pertains to a method for repairing or reconstructing a damaged or non-functioning muscle of a patient with enhanced innervation comprising the steps of:

a. acquiring a plurality of motor endplate-expressing muscle progenitor cells (MPCs) from a patient with a damaged muscle;
b. priming acquired MPCs by incubating said MPCs in the presence of an agent; and
c. introducing the primed MPCs to the damaged muscle of said patient.

In some illustrative embodiments, this present invention pertains to a method for repairing or reconstructing a damaged or non-functioning muscle of a patient with enhanced innervation disclosed herein, wherein said damaged or non-functioning muscle is a denervated head or neck muscle.

In some illustrative embodiments, this present invention pertains to a method for repairing or reconstructing a damaged or non-functioning muscle of a patient with enhanced innervation disclosed herein, wherein said damaged or non-functioning muscle is a denervated laryngeal muscle.

In some illustrative embodiments, this present invention pertains to a method for repairing or reconstructing a damaged or non-functioning muscle of a patient with enhanced innervation disclosed herein, wherein said damaged or non-functioning muscle is a denervated muscle involved in swallowing or voicing.

In some illustrative embodiments, this present invention pertains to a method for repairing or reconstructing a damaged or non-functioning muscle of a patient with enhanced innervation disclosed herein, wherein said MPCs are autologous-derived.

In some illustrative embodiments, this present invention pertains to a method for repairing or reconstructing a damaged or non-functioning muscle of a patient with enhanced innervation disclosed herein, wherein said damaged or non-functioning muscle is a denervated urinary detrusor bladder muscle.

In some illustrative embodiments, this present invention pertains to a method for repairing or reconstructing a damaged or non-functioning muscle of a patient with enhanced innervation disclosed herein, wherein said method provides a treatment for dysphagia.

In some illustrative embodiments, this present invention pertains to a method for repairing or reconstructing a damaged or non-functioning muscle of a patient with enhanced innervation disclosed herein, wherein said priming MPCs involves no genetic manipulation.

In some illustrative embodiments, this present invention pertains to a method for repairing or reconstructing a damaged or non-functioning muscle of a patient with enhanced innervation disclosed herein, wherein said priming MPCs is carried out in vitro to induce the creation of connections between nerve neurons and muscle fibers by incubating in the presence of an agent.

In some illustrative embodiments, this present invention pertains to a method for repairing or reconstructing a damaged or non-functioning muscle of a patient with enhanced innervation disclosed herein, wherein said agent comprises acetylcholine, neuregulin, agrin, or a combination thereof.

In some illustrative embodiments, this present invention pertains to a tool kit for repairing or reconstructing a damaged or non-functioning muscle of a patient with enhanced innervation comprising:

a. a plurality of moto endplate-expressing muscle progenitor cells (MPCs) acquired from a patient with a damaged muscle;
b. priming the acquired MPCs in vitro by incubating in the presence of an agent; and
c. introduction of the primed MPCs to the damaged muscle of said patient.

In some illustrative embodiments, this present invention pertains to a tool kit for repairing or reconstructing a damaged or non-functioning muscle of a patient with enhanced innervation disclosed herein, wherein said damaged or non-functioning muscle is a denervated head or neck muscle.

In some illustrative embodiments, this present invention pertains to a tool kit for repairing or reconstructing a damaged or non-functioning muscle of a patient with enhanced innervation disclosed herein, wherein said damaged or non-functioning muscle is a denervated laryngeal muscle, or a muscle involved in swallowing or voicing.

In some illustrative embodiments, this present invention pertains to a tool kit for repairing or reconstructing a damaged or non-functioning muscle of a patient with enhanced innervation disclosed herein, wherein said damaged muscle or non-functioning is denervated urinary detrusor bladder muscle.

In some illustrative embodiments, this present invention pertains to a tool kit for repairing or reconstructing a damaged or non-functioning muscle of a patient with enhanced innervation disclosed herein, wherein said tool kit is for the treatment of dysphagia.

In some illustrative embodiments, this present invention pertains to a tool kit for repairing or reconstructing a damaged or non-functioning muscle of a patient with enhanced innervation disclosed herein, wherein said priming MPCs is carried out in vitro to induce the creation of connections between nerve neurons and muscle fibers with no genetic manipulation involved.

In some illustrative embodiments, this present invention pertains to a tool kit for repairing or reconstructing a damaged or non-functioning muscle of a patient with enhanced innervation disclosed herein, wherein said agent comprises acetylcholine, neuregulin, agrin, or a combination thereof.

Restoration of movement of the paralyzed vocal fold has long been a goal of laryngologists treating vocal fold paralysis, but reports of successful restoration of vocal fold mobility have been quite limited. Purposeful vocal fold abduction and adduction have been achieved with reinnervation methods, but these procedures have not gained wide acceptance due to technical difficulty or donor site morbidity. The ideal procedure would restore mobility and laryngeal muscle mass in a high percentage of cases while being technically within the skillset of most otolaryngologists. Restoration of abductor movement would be particularly valuable for patients with bilateral vocal fold immobility, who often need a tracheostomy or other procedure for adequate airway.

Muscle progenitor cells (MPCs) (also called muscle stem cells) consist of satellite cells and myoblasts, and have the potential to increase muscle mass and to provide the stimulus for functional reinnervation when implanted into denervated muscles. MPCs can be derived from small samples of a patient's own tissue, and, thus, are not rejected by the immune system. They can be implanted into the laryngeal muscle by a simple injection, making this approach an attractive option for treating laryngeal paralysis.

While post-transplant muscle survival has been a major hurdle for tissue engineered skeletal muscle, we have discovered that our optimized technique of priming MPCs to express motor endplates significantly promotes both innervation and survival of the engineered muscle constructs to the point that the muscle thickness mimics that of the native adductor muscle complex. This discovery was made in a series of investigations focused on enhancing spontaneous reinnervation after recurrent laryngeal nerve (RLN) injury using MPCs.

First, we demonstrated that introduction of unmodified MPCs into an acutely denervated larynx results in attenuated atrophy, with no direct effect on innervation. Next, we discovered that certain factors, such as ciliary neurotrophic factor (CNTF), enhance survival of the MPCs while promoting spontaneous reinnervation of the acutely denervated larynx. On the other hand, we genetically programed MPCs with lentiviral vector to express CNTF, and found that injection of the CNTF-expressing MPCs into the adductor muscles after RLN injury led to enhanced spontaneous reinnervation when compared to the spontaneous reinnervation in controls. We initially contemplated incorporating these genetically modified MPCs into a hemilaryngeal MI, thereby potentially leading to an autocrine-mediated enhanced innervation of the MI post-implantation. However, use of genetically modified cells introduces tremendous regulatory and safety hurdles upon future clinical translation of such a model. To keep the model clinically translatable, we have discovered alternative in vitro approaches to promote post-implantation tissue engineered muscle innervation without involving genetic modification of the MPCs.

TABLE 1

Differentially Expressed mRNA in the PCA versus thyroarytenoid at one week after RLN transection

| UPREGULATED FACTOR | PCA FOLD: | *TA FOLD: | SUMMARIZED ROLE: |
|---|---|---|---|
| Cholinergic receptor, nicotinic $\alpha 1$ | 3.9 | 7.2 | Neuromuscular junction receptor |

Previously we found that the thyroarytenoid muscle complex receives greater spontaneous reinnervation than the posterior cricoarytenoid (PCA) muscle after recurrent laryngeal nerve (RLN) injury, and we identified over a 7-fold elevation in thyroarytenoid expression of motor endplate subunit (nicotinic cholinergic receptor $\alpha 1$) via microarray and RT-PCR analysis immediately preceding spontaneous reinnervation of the thyroarytenoid (Table I). Differentially expressed mRNA in the posterior cricoarytenoid (PCA) and the thyroarytenoid (TA) muscles at 1 week after recurrent laryngeal nerve (RLN) transection injury. TA and PCA expression (fold) is shown relative to sham TA and PCA, respectively, in a rat model. Denervated TA demonstrates elevation in nicotinic $\alpha 1$ receptor relative to sham TA (*$p<0.001$), and denervated PCA ($p<0.05$).

Figures 2A, 2B:
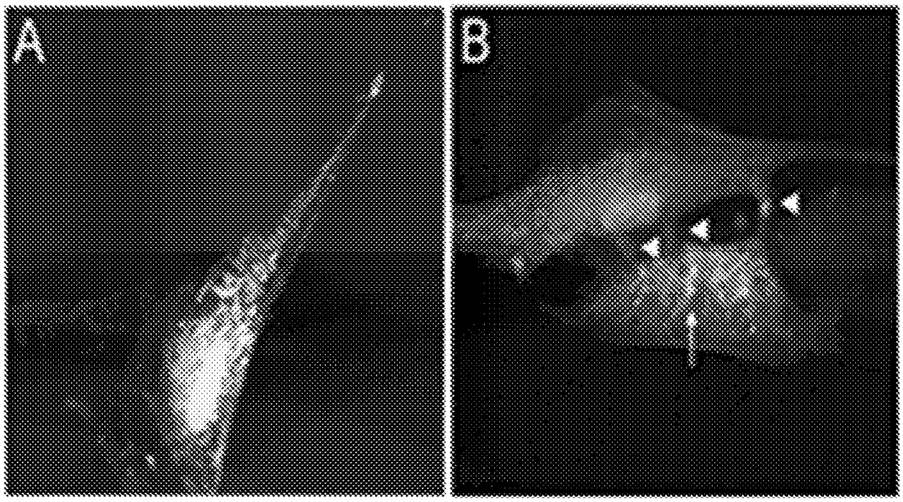
FIGS. 2A and 2B demonstrate MPC Formation of Motor Endplates.

We first investigated multiple approaches for inducing the MPCs to express nicotinic acetylcholine receptors. Our laboratory initially co-cultured motor neurons with MPCs, and discovered that we could successfully establish neuromuscular junctions in vitro, with motor endplates visible on the MPCs in co-culture (FIG. 1). Because it was technically challenging to separate and isolate the motor endplate-expressing MPCs from the co-culture habitat, we began investigating alternative approaches to induce MPCs to express motor endplates. We have identified and optimized a novel aneural culture method of "priming" MPCs to express motor endplates via incubating the MPCs with acetylcholine, neuregulin, and agrin (FIGS. 2A-2B) as the MPCs were differentiating into myotubes (MTs). FIGS. 2A-2B depict neuromuscular Junction Formation in Vitro within Co-cultures. Motoneurons are staining positive for motoneuron-specific choline acetyltransferase (ChAT) (light blue) and in areas where they are contacting the MPCs (light orange), the MPCs have formed motor endplates demarcated here in deep orange with motoneuron specific $\alpha$-bungarotoxin (arrows). Nuclei have been stained with DAPI (deep blue).

We then further investigated whether myopolymer constructs created with MPCs expressing motor endplates would receive greater innervation than control myopolymer constructs created from unmodified primary MPCs in a study comparing three myopolymer construct tissue engineering approaches. In brief, twenty F344 rats underwent resection of the left lateral thyroid cartilage with underlying adductor muscle [lateral and medial TA, alar cricoarytenoid (ACA), and the lateral cricoarytenoid (LCA) muscles] while taking care not to violate the inner mucosa. Animals were randomized to undergo repair with PCL polymer scaffolds alone (n=5) [PCL group], muscle stem cell (MSC) muscle-polymer constructs (n=5) [MSC group], myotube (MT) based muscle-polymer constructs (n=5) [MT group], or motor endplate-expressing (MEE) based muscle-polymer constructs (n=5) [MEE group]. At one month, we found that the MEE group demonstrated the greatest muscle thickness and strongest innervation based on EMG activity and the percentage of motor endplates with nerve contact (see Table 2, FIG. 3, and FIGS. 4A-4F).

TABLE 2

Post-Implantation Tissue Engineered Muscle Innervation: Innervation Status and Muscle Thickness at one month

| | Mean Motor Endplate Count | % Motor Endplates with Nerve Contact | Mean Tissue Engineered Muscle Thickness (μm) |
|---|---|---|---|
| MSC Group | 82.6 | 82.4% | 587.3 |
| MT Group | 44.3 | 65.8% | 680.2 |
| MEE Group | 87.3 | 94.8%* | 750.3* |

As shown in Table 2, the MEE group showed the greatest innervation at one month based on the percentage of motor endplates with nerve contact. The MEE group also demonstrated the greatest viable muscle thickness (based on axial section measurements); *$p<0.05$.

Figure 3:
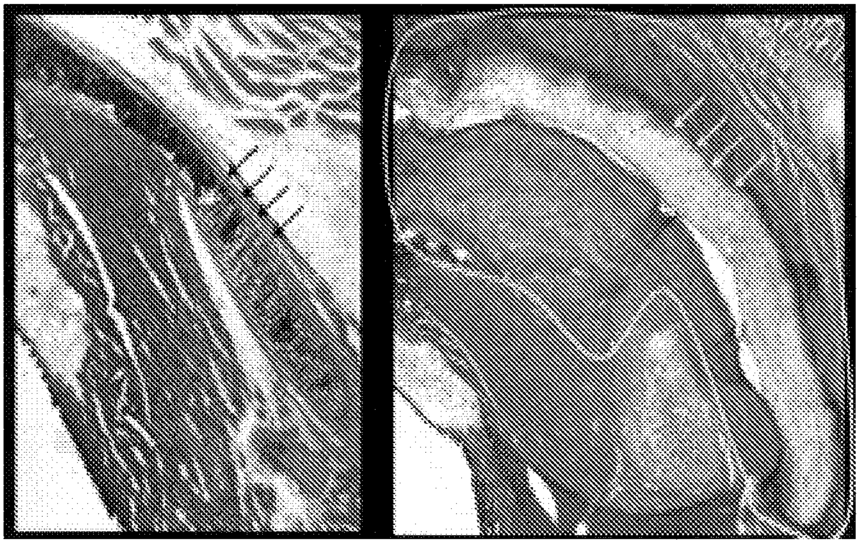
FIG. 3 depicts tissue engineered muscle-polymer constructs for the larynx. The left image is an axial H&E stained section (12 μm) of the native rat hemilarynx with the thyroid cartilage intact (arrow) (40× phase contrast microscopy). The right image shows rat hemilarynx one month after hemilaryngeal resection of thyroid cartilage and muscle, and repair with an MEE tissue engineered muscle/polymer construct. The stem cell-based muscle is circled, and arrows demarcate the PCL polymer scaffold.
Figure 4A:
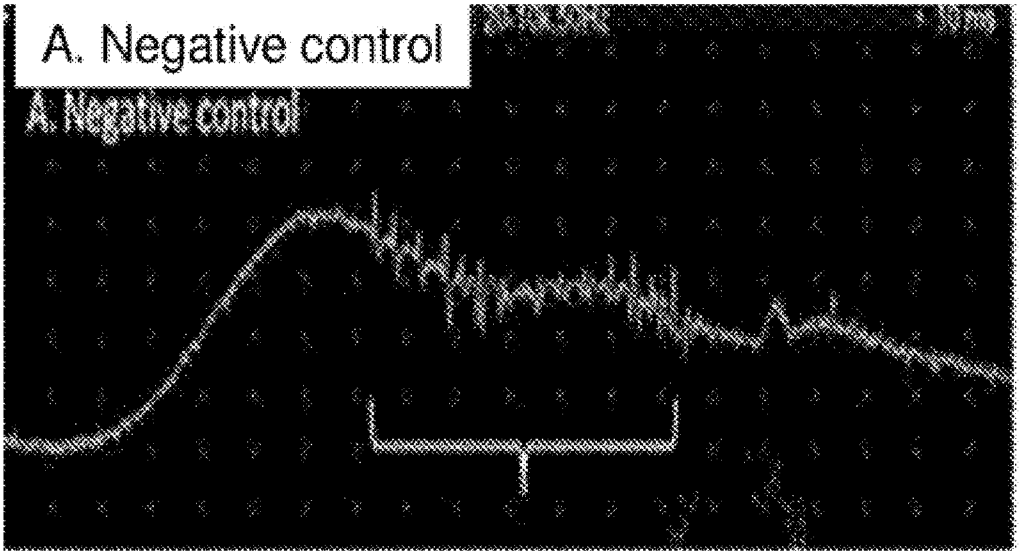
FIGS. 4A-4F show representative laryngeal electromyography (LEMG) findings. To detect relative differences in activity levels, LEMG tracings were recorded with an amplitude=50 μV and sweep speed=10 ms (A-E). To demonstrate inspiratory firing of the posterior cricoarytenoid (PCA), the tracing was recorded at amplitude=50 μV and sweep speed=100 ms (F).
Figure 4B:
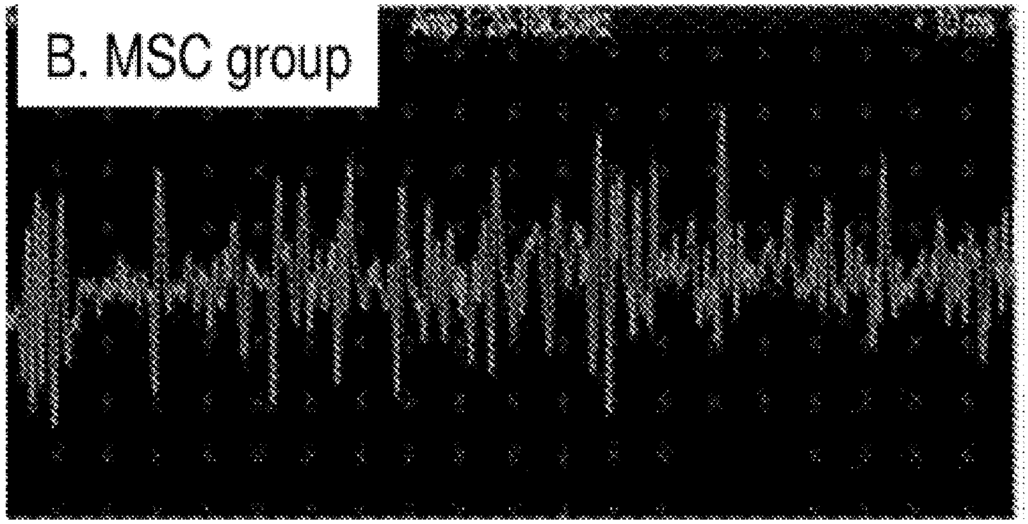
Figure 4C:
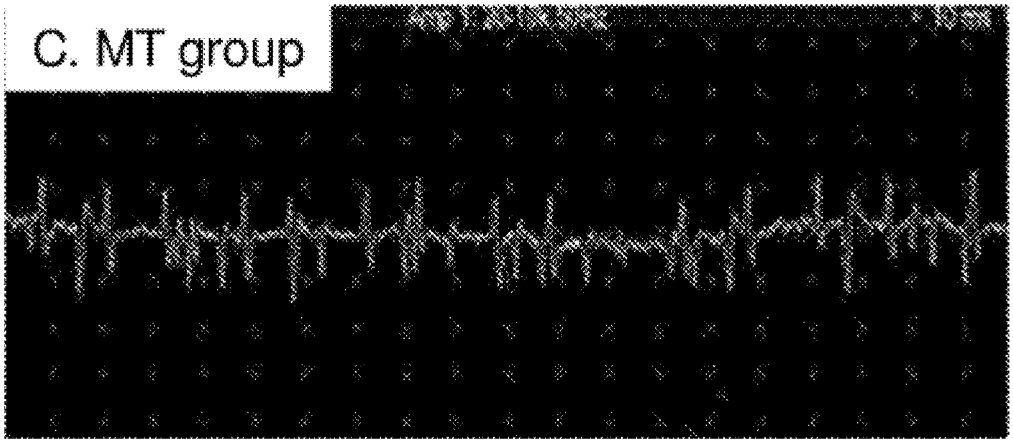
Figure 4D:
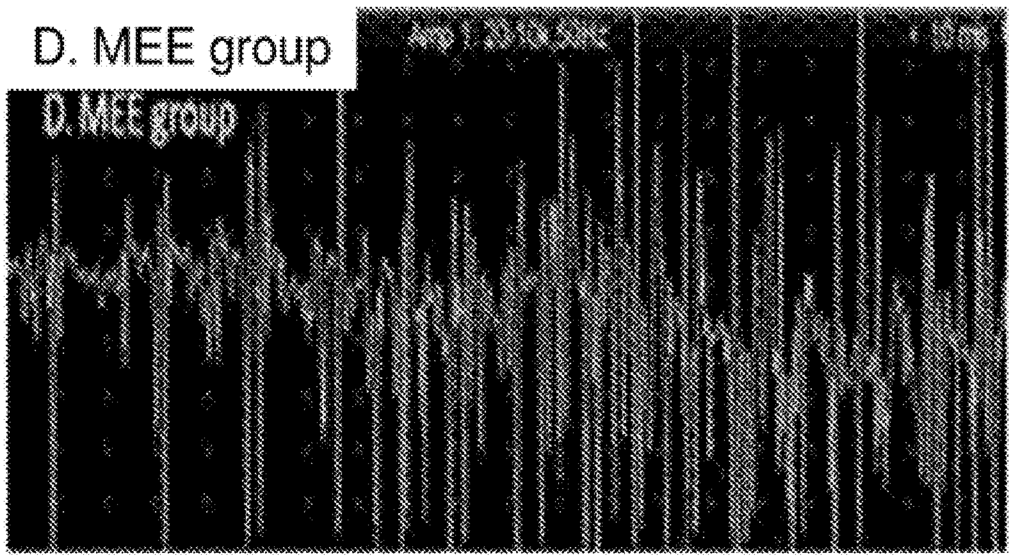
Figure 4E:
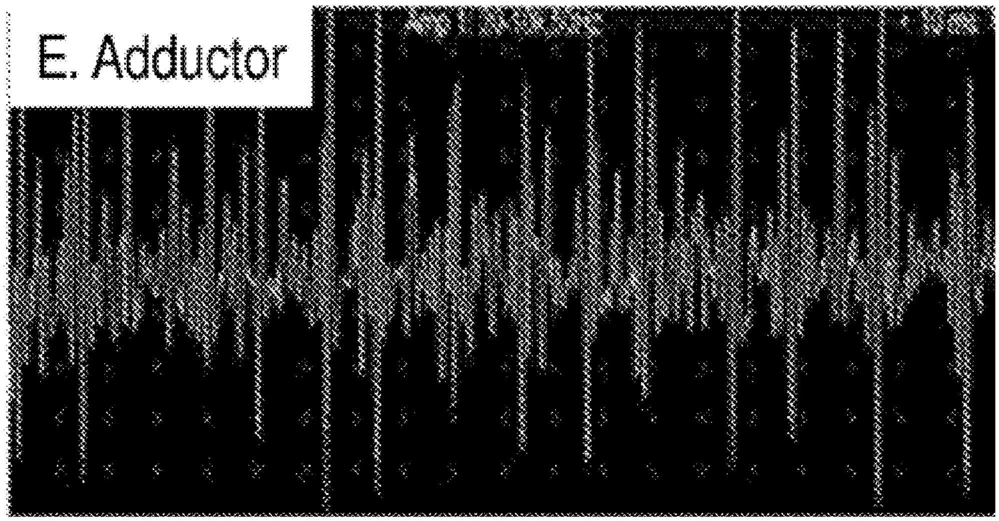
Figure 4F:
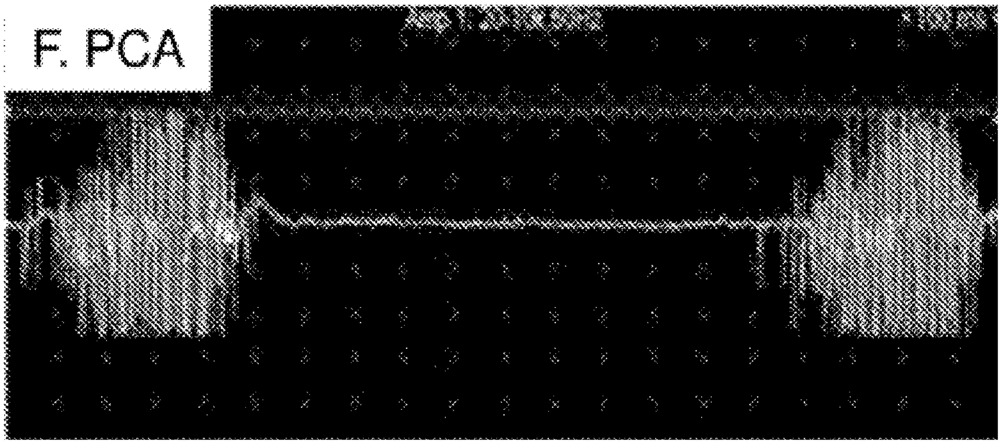
Figure 5A:
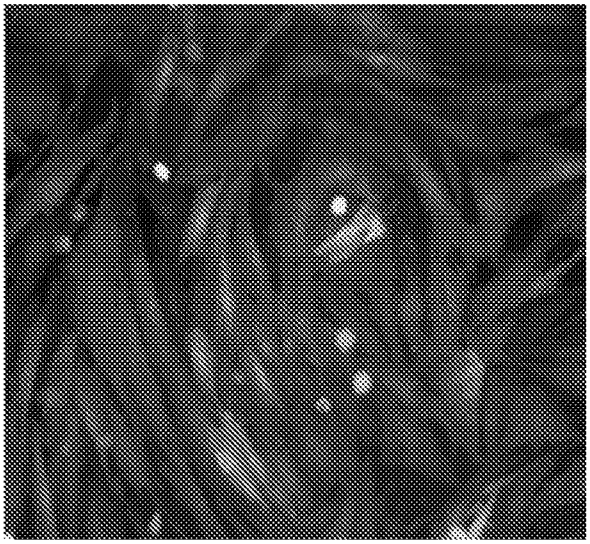
FIGS. 5A-5B depict Dog 1 MPCs in culture under fluorescent microscopy.
Figure 5B:
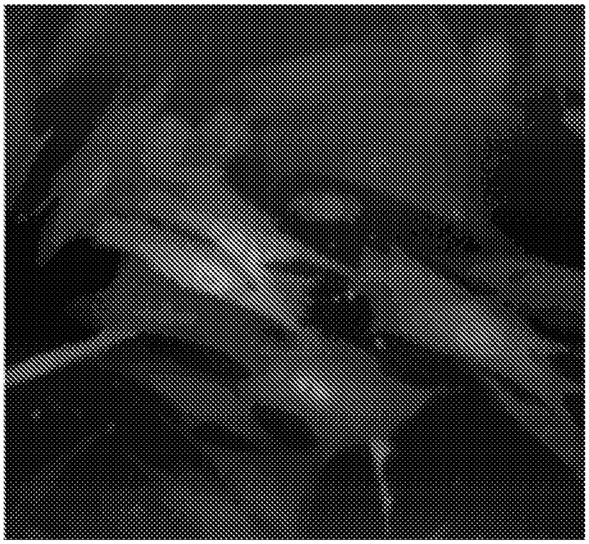
Figure 6A:
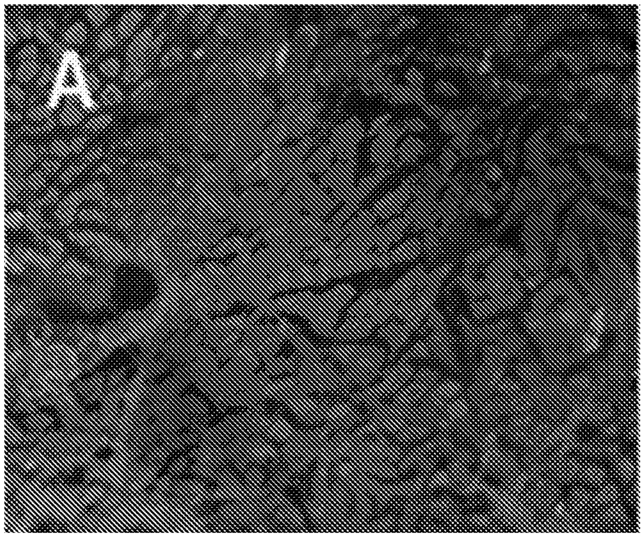
FIGS. 6A-6D show Dog 1 muscle fiber specimen (14 μm section thickness) imaged at 10× magnification (left) with magnified immunohistochemistry (IHC) views (right).
Figure 6B:
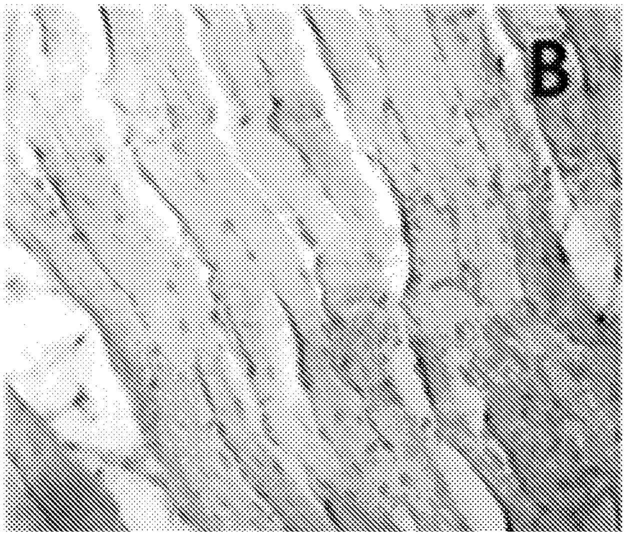
Figure 6C:
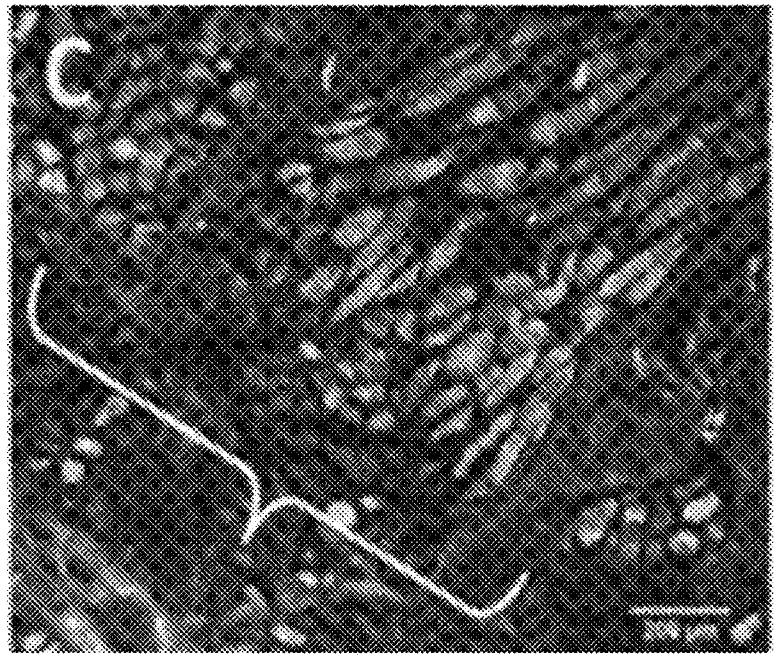
Figure 6D:
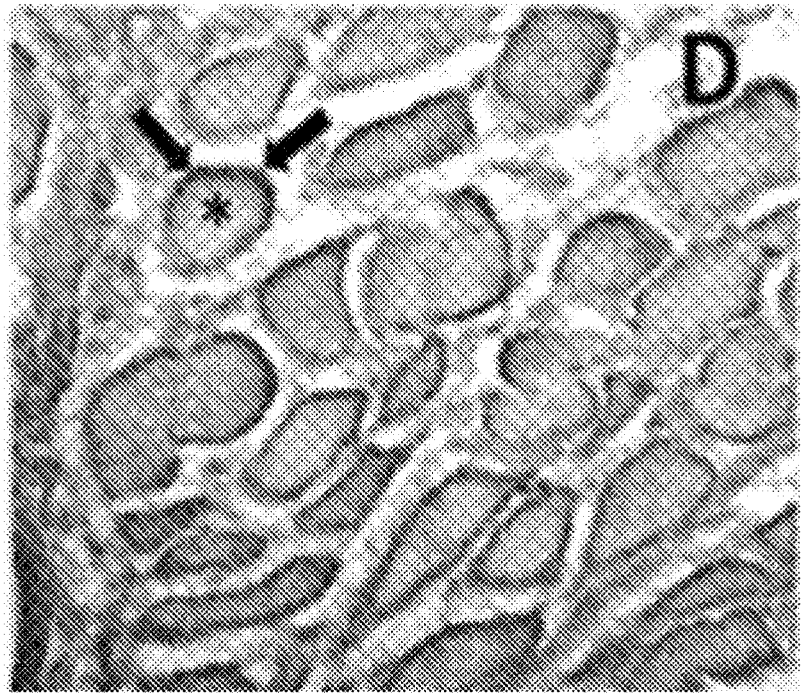

FIG. 3 depicts tissue engineered muscle-polymer constructs for the larynx. The left image is an axial H&E stained section (12 μm) of the native rat hemilarynx with the thyroid cartilage intact (arrow) (40× phase contrast microscopy). The right image demonstrates the rat hemilarynx one month after hemilaryngeal resection of thyroid cartilage and muscle, and repair with an MEE tissue engineered muscle/polymer construct. The stem cell-based muscle is circled, and arrows demarcate the PCL polymer scaffold.

FIGS. 4A-4F show representative laryngeal electromyography (LEMG) findings. To detect relative differences in activity levels, LEMG tracings were recorded with an amplitude=50 μV and sweep speed=10 ms (A-E). To demonstrate inspiratory firing of the posterior cricoarytenoid (PCA), the tracing was recorded at amplitude=50 μV and sweep speed=100 ms (F). (FIG. 4A) In the negative PCL control, no active motor unit potentials were detected due to the absence of significant tissue engineered muscle on the implant; insertional activity was reproducible (bracket) when the EMG recording needle was inserted directly into the PCL implant suggesting sparsely populated non-innervated muscle cells had infiltrated the scaffold. (FIG. 4B) The MSC group demonstrated low levels of motor unit potentials that fired in synchrony with the contralateral adductor muscle, and no inspiratory activity. (FIG. 4C) The MT group demonstrated qualitatively less recruitment upon laryngospasm and no inspiratory activity. (FIG. 4D) The MEE group demonstrated bursts of motor unit potentials that were firing with intensity and timing similar to that of the contralateral native adductor muscle complex, and without inspiratory activity. (FIG. 4E) The native adductor muscle complex demonstrates bursts of motor unit potentials during laryngospasm, with no active firing on inspiration. (FIG. 4F) The PCA demonstrates characteristic inspiratory bursts of activity which were absent in the native adductor complex and the tissue engineered muscle.

Additionally, we extended our investigation to a large animal dog model. A dog has a larynx more similar to that of the human, and functional measures of motor strength could be assessed after MPCs are therapeutically introduced into a denervated thyroarytenoid muscle.

Materials & Methods

Three purpose-bred mongrel hounds weighing about 20 kg were obtained and housed in a facility approved by the American Association for Accreditation of Laboratory Animal Care. The study was performed in accordance with the PHS Policy on Humane Care and Use of Laboratory Animals, the NIH Guide for the Care and Use of Laboratory Animals, and the Animal Welfare Act (7 U.S.C. et seq.); the animal-use protocol was approved by the Institutional Animal Care and Use Committee of Washington University School of Medicine.

Initial Procedure—Baseline Data and Muscle Harvest

Under general anesthesia, a midline incision exposed the larynx and trachea. A tracheostomy was made between rings 8-12 as previously described (Dahm, et al., Otolaryngol Head Neck Surg. 1998, 118: 376-380). Both recurrent laryngeal nerves (RLNs) were dissected, fitted with Harvard electrodes, and connected to a custom constant-current laryngeal nerve stimulator.

Pretreatment baseline laryngeal adductor function was measured in two ways (Paniello, et al., *Ann Otol Rhinol Laryngol.* 2017, 126:173-178). First, laryngeal LAPs were determined as previously described. Briefly, the cuff of an endotracheal tube is connected to a pressure transducer, and the tube is passed between the vocal folds while the RLN is stimulated at supramaximal current. Pressure measurements are made at each frequency from 20-100 Hz at 10 Hz intervals, and the unstimulated baseline pressure is subtracted. Laryngeal adductor muscles reach tetany at higher frequencies (70-100 Hz). Second, GCF was measured as previously described. Briefly, a suture is passed through a lateral minithyrotomy, through the ventricle, around the vocal process and back, forming a loop that is hooked onto a force gauge. The RLN is stimulated as described above and the force is recorded. The GCF and LAP have been shown to be highly correlated.

Under an operating microscope, each recurrent laryngeal nerve (RLN) was transected 5 cm inferior to the cricothyroid joint and then immediately repaired using 9-0 nylon sutures for epineural anastomosis. A 3~4 gram portion of sternocleidomastoid muscle was harvested and placed in initial myogenic culture medium [F-10 medium (Gibco, Grand Island. New York; 11550-043), 20% fetal bovine serum (HyClone Laboratories, Thermo Fisher Scientific, Waltham, Massachusetts; SH30070.03), 1% penicillin/streptomycin/amphotericin B (Cellgro; Mediatech, Inc, Manassas, Virginia; 30-004-CI), and 1% chicken embryo extract (SeraLab, Haywards Heath, England; CE-650-J)]. The stoma was matured, the wound was closed and the dog recovered. The muscle sample was same-day shipped on ice to the Halum cell culture laboratory for derivation of MPCs.

MPC Cultures

The MPC culture techniques were followed as previously described (Halum, et al., *Laryngoscope* 2008, 118: 1308-1312). Briefly, the muscle sample was minced into small pieces and incubated in 0.2% collagenase type I (Worthington Biochemical Corp, Lakewood, New Jersey; LS004214) in a shaker at 37° C. for 2 hours. Digested tissue was subjected to rigorous pipetting to dissociate fibers, and then filtered through a 100 nm pore-size strainer. The pellet was suspended in initial myogenic culture medium and seeded into a gelatin coated T25 flask. Fresh medium was added every other day. When primary cultures reached 70% confluency, they were passaged to prevent myotube formation. After the second passage the growth medium was changed to a myogenic culture medium (F-10 medium Gibco, Grand Island. New York; 11550-043), 10% fetal bovine serum (HyClone Laboratories; SH30070.03) and 1% penicillin/streptomycin (HyClone Laboratories; J110381)).

Cells were labeled for subsequent identification in one of two ways. For dog 1, MPCs were transduced with green fluorescent protein (GFP)-expressing lentiviral vector at passage 2 in the presence of 8 μg/mL protamine sulfate (Sigma-Aldrich, p4020). For dogs 2 and 3, the MPCs were incubated with the fluorescent marker QTracker 565 (Molecular Probes; Q25001MP) for 60 minutes at 37° C. After incubation, the cells were washed twice with complete growth medium. Label uptake was confirmed with fluorescent microscopy.

To induce motor endplate expression (dog 3), acetylcholine chloride (40 nmol/L; Tocris Bioscience, Bristol, England; 2809), agrin (10 nmol/L; R&D Systems, Minneapolis, Minnesota; 550-AG), and neuregulin (2 nmol/L; R&D Systems; 378-SM), was added to culture medium and the culture continued for 7 days. These MPCs are referred to as motor endplate enhanced cells (MEEs). When the cultures reached approximately $10^7$ cells (within 4-5 weeks) they were shipped on ice back to the canine laryngeal physiology lab at Washington U.

Second Procedure—MPC Implantation

The MPCs were washed several times in PBS, then spun gently into a pellet with a volume of 0.5 cc. The dog was placed under general anesthesia, intubated using the permanent stoma. Direct laryngoscopy was performed and the scope was suspended. An 18G angiocatheter was passed through the skin, through the cricothyroid membrane, and into the thyroarytenoid muscle. The MPC syringe was attached and the cells were implanted, followed by a 0.5 cc flush of normal saline. The dog was awakened and recovered.

Third Procedure—Final Data Collection

The first experiment (dog 1) was carried out only to confirm success of the process and viability of the transferred MPCs; the dog was euthanized 2 weeks following MPC implantation and the larynx was harvested for histologic study.

Long term functional experiments were carried out for dogs 2 and 3. Six months after nerve transection and repair (5 months post-MPC implantation), the awake dog was examined for spontaneous vocal fold motion by inserting a scope through the tracheostomy and visualizing the vocal folds from below ("infraglottic exam"). Vocal fold movement was induced by introducing a few cc's of water into the mouth from a syringe, causing the dog to swallow. Movement was scored on a scale of 0 (no movement) to 4 (complete adduction).

Next, the dog was anesthetized and the neck opened in the midline. Each RLN was dissected and an electrode placed 10 cm inferior to the cricothyroid joint. Direct laryngoscopy was performed and the stimulated motion of the vocal folds was observed, video recorded and scored on the same 0-4 scale. LAP and GCF were measured as described above. The larynx was then harvested, placed in 4% paraformaldehyde and shipped to the Halum lab.

Histological and Immunohistochemistry (IHC) Analysis

Larynges were fixed with 4% paraformaldehyde in PBS for 24 hours, then changed to 30% sucrose in PBS solution until tissues sunk to the bottom. Cryo-embedded sections were cut at a thickness of 12-14 μm with the cryotome. Standard hematoxylin and eosin (H&E) staining was performed. For GFP analysis, unstained frozen sections were evaluated under fluorescent microscopy to evaluate for areas of green fluorescence, and IHC was performed with anti-GFP antibody to ensure the green fluorescence represented GFP (not nonspecific fluorescence).

For additional analysis of the motor endplates (staining with βIII tubulin) with neuronal contact (staining with α-bungarotoxin) sections were permeabilized with Triton X-100 for 20 minutes at room temperature and then blocked with 1% BSA for 1 hour. Sections were then incubated with AlexaFluor 493 conjugated βIII tubulin antibody (1:10) and AlexaFluor 647 conjugated α-bungarotoxin (1:1000) overnight at 4° C., then examined by fluorescent microscopy.

Results

MPCs were successfully isolated and cultured from all 3 dogs. Dogs 1 and 2 were implanted with $10\times10^6$ MPCs; dog 3 received $12\times10^6$ MEEs. MPCs were successfully cultured from all dogs. Laryngeal adductor force measurements averaged 60% of their baseline pre-treatment values in non-implanted controls, 98% after implantation with MPCs, and 128% after implantation with motor endplate-enhanced MPCs. Histology confirmed the implanted MPCs survived, became integrated into thyroarytenoid muscle fibers, and were in close contact with nerve endings, suggesting functional innervation. MPCs were shown to significantly enhance adductor function in this pilot canine study. Patient-specific MPC implantation could potentially be used to improve laryngeal function in patients with vocal fold paresis/paralysis, atrophy, and other conditions. Further experiments are planned.

Histology and Immunohistochemistry

Figure 7A:
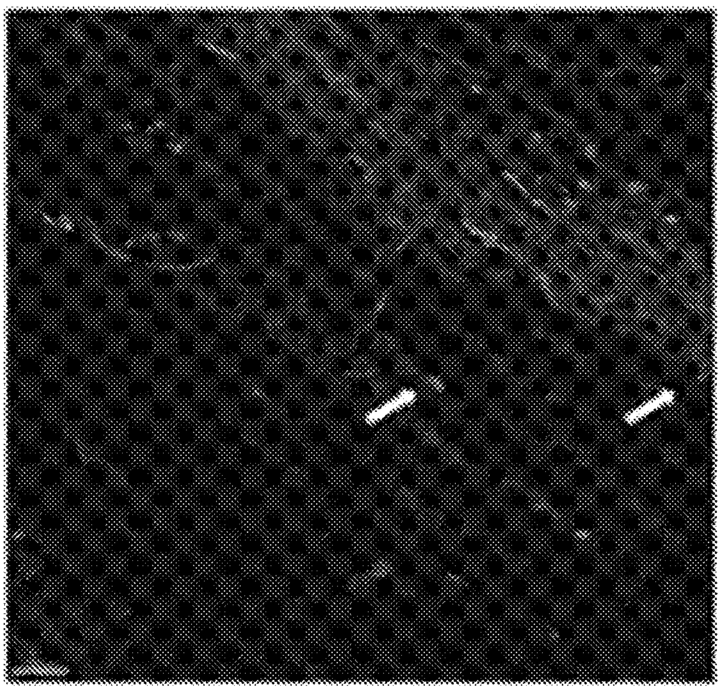
FIGS. 7A-7C depict Dog 3 muscle fiber specimen (12 μm section thickness) imaged at low magnification with immunohistochemical analysis demonstrating motor endplates stained with bungarotoxin in red (depicted with white arrows) and neuron specific beta3-tubulin in green.
Figure 7B:
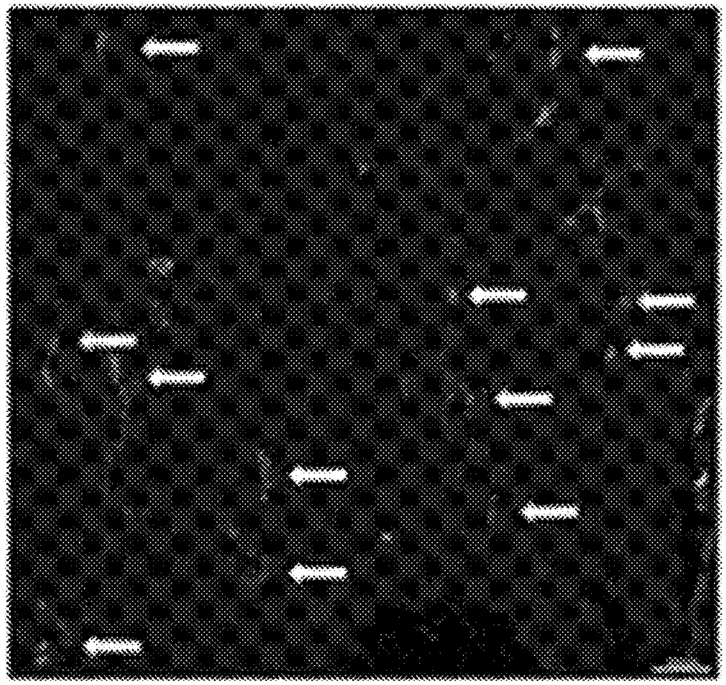
Figure 7C:
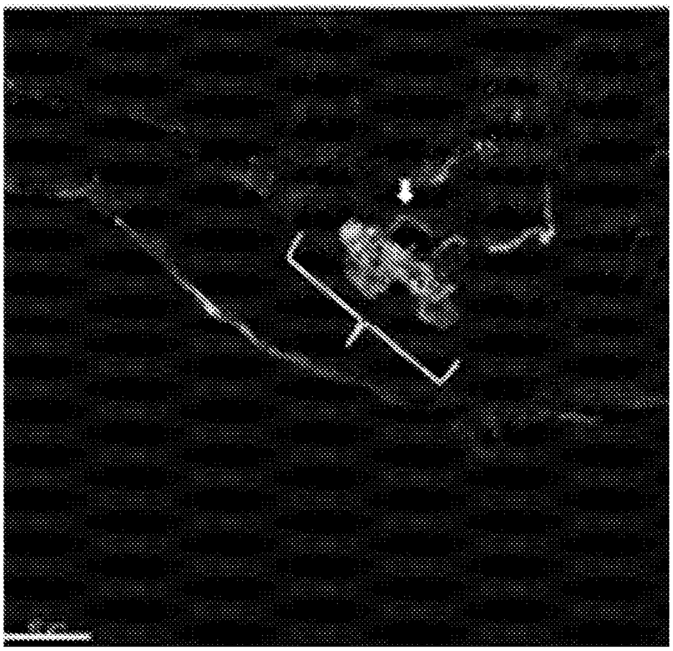
Figure 8A:
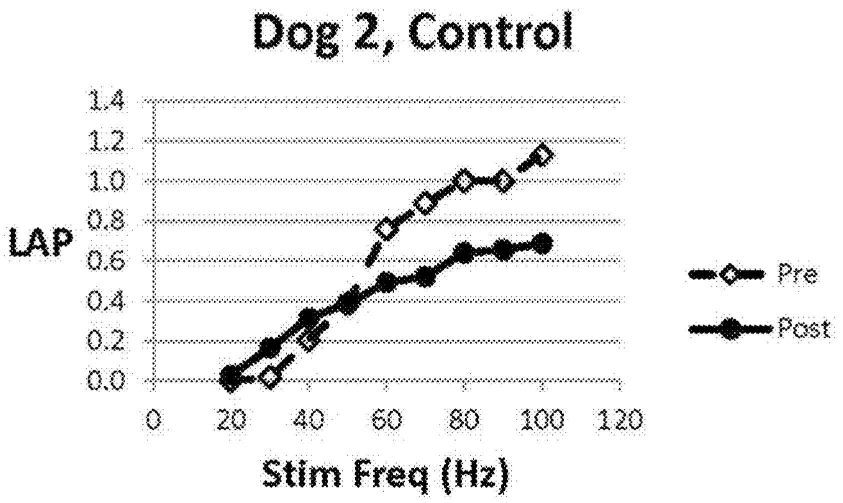
FIGS. 8A-8D show laryngeal adductor pressure (LAP) curves for dogs 2 and 3.
Figure 8B:
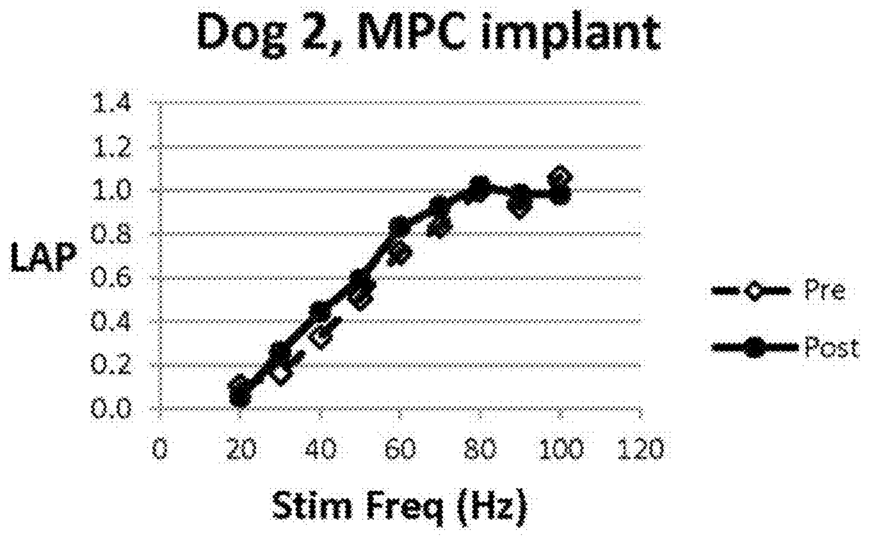
Figure 8C:
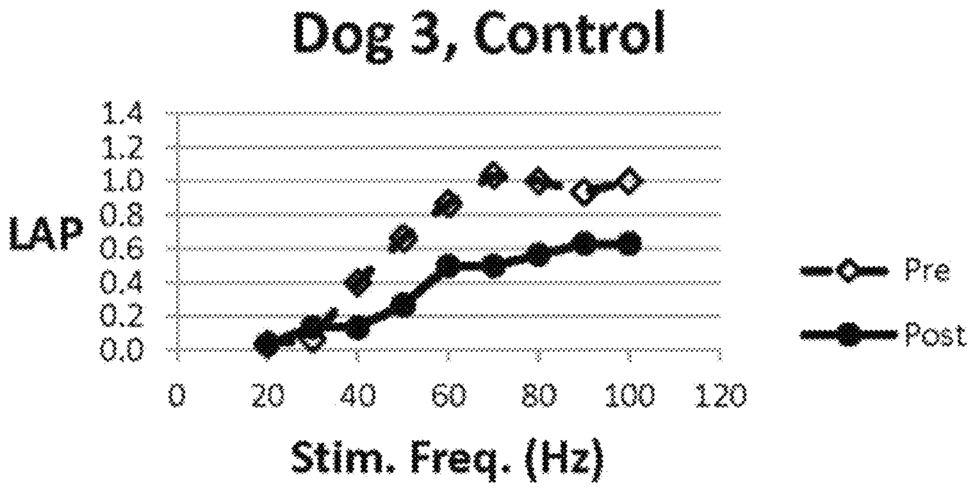
Figure 8D:
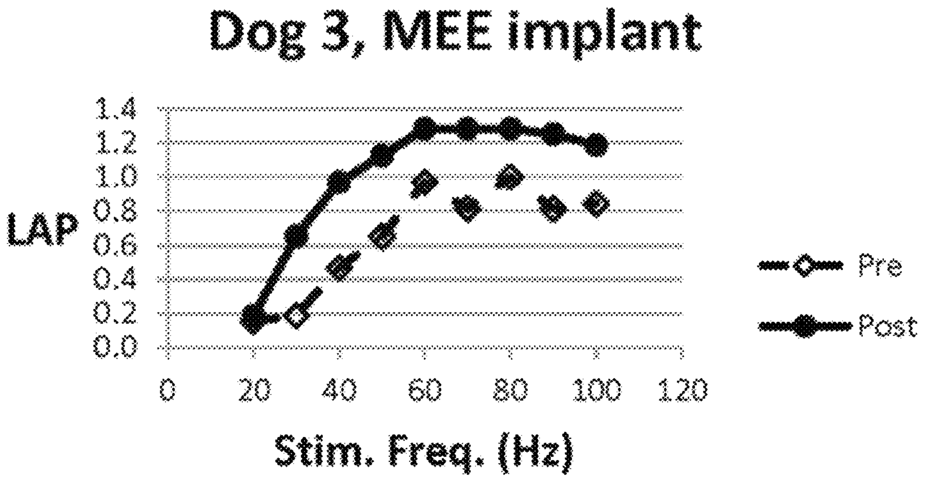

The GFP and QTracker 545 fluorescent labels were present in a high fraction of the cultured cells, as seen on fluorescent microscopy (FIGS. 5A-5B, 6A-6D, and 7A-7C). In the harvested thyroarytenoid muscles, the fluorescent labels showed good survival of the implanted MPCs, with no label seen in the non-injected control muscles (FIGS. 6A-6D, and 7A-7C). The muscle fibers that had MPCs incorporated tended to have larger diameters than the non-labeled fibers in all three dogs. The animal receiving the MEEs demonstrated areas of dense motor endplate expression with complexes of motor endplates which were fully innervated based on neuronal contact (FIGS. 7A-7C).

Functional Measures (Dogs 2 and 3)

Spontaneous adduction during swallow was seen in the right (MPC injected) vocal fold of both dogs, but not on the left (control) side. When the RLNs were stimulated with supramaximal constant current, movement was seen in both vocal folds, but with a significantly more normal range of motion on the MPC side (Table 3).

TABLE 3

Functional measurements from dogs 2 and 3.

| | | | | | Vocal Fold Movement | |
|---|---|---|---|---|---|---|
| | | Injected | LAP | GCF | Spont. | Induced |
| Dog 2 | Rt | MPCs | 0.98 | 1.00 | 3 | 4 |
| | Lt | saline | 0.63 | 0.67 | 0 | 2 |
| Dog 3 | Rt | MEEs | 1.28 | 1.44 | 4 | 4 |
| | Lt | saline | 0.60 | 0.55 | 1 | 2 |

The measures of vocal fold adductor strength, LAP and GCF, both showed significantly more recovery in the MPC injected side than the control side (FIGS. 8A-8D). The MPCs implanted in dog 2 led to a recovery of adductor strength to normal (pre-treatment) levels by both measures; the saline control had typical recovery for the transection-repair nerve injury model. Dog 3 received motor endplate-enhanced cells, and recovered adductor strength to 28% higher than normal (by LAP); the GCF measure was even higher. These results are summarized in Table 3 (above). Laryngeal adductor pressure (LAP) and glottic closing force (GCF) results expressed as proportion of pre-treatment measures. Dogs were implanted with autologous cultured muscle progenitor cells (MPCs) or MPCs with enhanced motor endplate expression (MEEs). Movement scores on scale of 0 (no movement) to 4 (normal movement).

In this limited pilot study, implantation of autologous-derived muscle progenitor cells into denervated thyroarytenoid muscle resulted in greater functional reinnervation than similar experiments without these cells. More significantly, purposeful adduction of the vocal fold was observed with a glottic closure reflex on swallow. This effect appears to be due to both increased muscle mass, as evidenced by increased myofiber diameter, as well as increased innervation (based on motor endplate-to-nerve contact), with a further increase when motor endplate expression was enhanced in dog 3. These data support the idea of MPC implantation in the treatment of patients with recurrent laryngeal nerve (RLN) injury.

The procedure to implant these cells is fairly simple and should be within the skillset of any ololaryngologist that performs vocal fold injections. Implantation of autologous-derived muscle progenitor cells was found to significantly increase adductor strength in a canine model of RLN transection and repair, which validates this approach as a potential new therapy for vocal fold paralysis.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A method of priming motor endplate-expressing muscle progenitor cells (MPCs) for a cell therapy for treating a patient with a damaged or non-functioning muscle, comprising a) acquiring a plurality of motor endplate-expressing muscle progenitor cells (MPCs) from a patient with a damaged or non-functioning muscle;

b) preparing a composition of the MPCs that does not comprise a scaffold;

c) priming the MPCs in vitro with a therapeutically effective amount of a composition comprising acetylcholine, neuregulin, and agrin; and optionally d) subjecting the MPCs in the composition made in step c) to genetic manipulation.

2. The method of claim 1, wherein the MPCs are autologous-derived.

3. The method of claim 1, wherein the MPCs are primed with no genetic manipulation.

4. The method of claim 1, wherein the MPCs are primed to induce the creation of connections between nerve neurons and muscle fibers.

5. The method of claim 1, wherein the primed MPCs integrate with damaged and non-functioning muscle's fibers and are in close contact with nerve endings.

6. The method of claim 1, wherein the cell therapy is carried out through minimally invasive, non-surgery injection directly to the site of damaged or non-functioning muscle.

7. A method of performing a cell therapy in a patient in need thereof with the primed MPCs of claim 1, wherein said composition comprising the primed MPCs does not contain an artificial supporting scaffold, comprising the step of administering a therapeutically effective amount of the composition comprising the primed MPCs to the site of a damaged and non-functioning muscle in the patient, thereby repairing the damaged and non-functioning muscle.

* * * * *